United States Patent [19]
Maki, Jr.

[11] Patent Number: 6,112,599
[45] Date of Patent: Sep. 5, 2000

[54] METHOD AND APPARATUS FOR MEASURING A CEMENT SAMPLE USING A SINGLE TRANSDUCER ASSEMBLY

[75] Inventor: Voldi E. Maki, Jr., Austin, Tex.

[73] Assignee: Cement Test Equipment, Inc., Tulsa, Okla.

[21] Appl. No.: 09/048,292

[22] Filed: Mar. 26, 1998

[51] Int. Cl.[7] .................................................. G01N 29/00
[52] U.S. Cl. .................................. 73/801; 73/587; 73/627
[58] Field of Search .............................. 73/801, 587, 597, 73/598, 600, 620, 627

[56] References Cited

U.S. PATENT DOCUMENTS

| | | |
|---|---|---|
| 4,259,868 | 4/1981 | Rao et al. . |
| 4,377,087 | 3/1983 | Rodot . |
| 4,567,765 | 2/1986 | Rao et al. . |
| 4,571,693 | 2/1986 | Birchak et al. . |
| 4,862,384 | 8/1989 | Bujard . |
| 5,412,990 | 5/1995 | D'Angelo et al. . |

OTHER PUBLICATIONS

D. T. Mueller, et al.: "Characterization of the Initial, Transitional, and Set Properties of Oilwell Cement," SPE 36475, 1996, pp. 613–616.

L. L. Lacy, et al.: "Analyzing Cements and Completion Gels Using Dynamic Modulus," SPE 36476, 1996, pp. 625–630.

*Primary Examiner*—Max Noori
*Attorney, Agent, or Firm*—Browning Bushman

[57] ABSTRACT

A sample-holding container having a structure that may be heated and internally pressured with water to subject the sample to its anticipated working conditions as the sample is tested. A single, oil-encapsulated transducer transmits acoustic energy waves through a chamber containing the sample and receives reflections of the waves from the chamber floor. The transducer converts the received reflected acoustic waves to an electrical signal that is analyzed to evaluate the sample. Pressurized water in contact with the sample is employed in the chamber to pressurize the sample during the test. A movable, pressure-responsive barrier between the oil encapsulating the transducer and the water pressurizing the sample maintains the transducer and the sample at the same pressure. A thin membrane between the transducer and the sample permits the transducer to be in physical contact with the sample while protecting the transducer from chemical exposure. Pressure differentials across sensitive components are prevented with a self-resetting pressure relief system. The sample material may be a cement slurry with the speed of the acoustic energy waves traveling through the sample and reflected back to the transducer being analyzed to determine the compressive strength of the cured cement. Acoustic energy signal optimization is achieved by maintaining the transducer in contact with the sample, limiting the emitted acoustic energy wave to a primary signal, calibrating the transducer with the chamber, detecting abnormal pressure conditions and fluid movement, and preventing pressure differentials from developing across sensitive components during a pressure leak.

26 Claims, 5 Drawing Sheets

METHOD AND APPARATUS FOR MEASURING A CEMENT SAMPLE USING A SINGLE TRANSDUCER ASSEMBLY

BACKGROUND OF THE INVENTION

1. Field of the Invention

The present invention relates to methods and apparatus for testing material samples. More specifically, the present invention relates to methods and apparatus for determining the cured compressive strength and other characteristics of a cement slurry sample.

2. Description of the Prior Art

Cement is used at different times during the drilling, completion, and repair of wells to bond the well casing pipe into the wellbore, to seal off portions of the subsurface formation from the wellbore, to repair damage in a cased or uncased well, and for various other purposes. Generally, the cement is pumped into the well as a relatively low viscosity slurry. After the cement slurry is in place, it hardens to a solid state. Throughout these various construction and repair procedures, it is important that the cement retain a sufficiently low viscosity as it is being moved into place within the well or formation. It is also necessary that the strength and physical characteristics of the hardened or cured cement be adequate to perform the intended functions in the well.

The curing time and the viscosity change during the curing of cement are dependent upon the materials used in forming the cement slurry, the method used in preparing and injecting the material, and the environmental conditions of the subsurface site. Before undertaking a cement injection procedure, it is essential to know that the pumping and setting characteristics and other physical attributes of the cement to be injected into the well are within design requirements for the specific site.

Initial methods of testing a particular composition of cement required testing viscosity changes of the curing sample over a period of time and destructively testing cured samples of the cement for compression strength. These techniques were superseded by the development of methods and apparatus for evaluating the sample by propagating acoustic energy waves through the uncured sample and evaluating the speed of travel of the waves through the sample to obtain information about the curing time and compressive strength of the cured cement. The background of ultrasonic testing and the devices used in such testing for determining characteristics of structural concrete are described in a paper entitled "Characterization of the Initial, Transitional and Set Properties of Oilwell Cement," Society of Petroleum Engineers paper SPE 36475, 1996. A related publication, SPE 36476, entitled "Analyzing Cements and Completion Gels Using Dynamic Modulus," 1996, describes the theory, design, and operation of an ultrasonic apparatus that measures the dynamic modulus of cements and gels. One of the early systems employed to ultrasonically test cement is described in U.S. Pat. No. 4,259,868, to Rao et al., issued in 1981.

Various sample-holding containers have been employed to hold the cement slurry sample during the performance of sonic tests. One such container, which also permits the sample to be pressurized and heated, is described in U.S. Pat. No. 4,377,087, issued in 1983 to Francois Rodot. The Rodot patent describes a sample-holding device that employs two electro-acoustic transducers that are positioned across from each other to measure the transit time of a sonic signal traveling from one transducer to the other through the sample slurry. The information derived from the test is used to determine the setting and hardening characteristics of the cement sample.

The sample-holding device of the Rodot patent places the transmitting and receiving transducers in intimate contact with the cement slurry sample. A flexible diaphragm covers the top of the slurry sample within the sample chamber. A pressure line on the opposite side of the diaphragm supplies a pressurizing fluid to the sample chamber, which in turn pressurizes the cement sample.

An alternative holder described in the Rodot patent employs oil as a pressurizing medium. During the filling and testing process, the sample-holding apparatus must be maintained in a fixed orientation to prevent the cement sample from escaping the testing chamber.

Both of the sample-holding devices described in the Rodot patent require the oil to surround the electro-acoustic transducers with the oil being in direct contact with the cement sample. Each time a sample is tested, the oil-containing portion of the container must be refilled with oil to ensure uniform pressure in the sample and on the transducers.

Where large pressures are to be applied to the sample, or where the transducer can be adversely affected by large pressure differentials acting across its structure, it becomes critical to protect the transducers from pressure extremes that may occur during the testing procedure. In this regard, leakage past a flexible seal or other failure that prevents proper pressure equalization between the pressured cement and the transducer body can prevent proper operation of the transducers during the testing process and can also severely damage the transducer.

Another danger that becomes increasingly threatening as the testing pressures are increased is that of water leaking into contact with the transducer's electrical conductors. The existence of such leakage can prevent the transducer from functioning properly and can produce faulty readings in the equipment that analyzes the signals transmitted from the transducer.

In sonic testing procedures, where received acoustic energy waves are analyzed to determine characteristics of the medium through which the waves travel, knowledge about the wave path becomes critically important. If the generating transducer produces acoustic energy waves that radiate from different areas of the transducer, the received signal may be a combination of signals traveling over different paths. The result is a complex signal that is difficult to correctly analyze. For purposes of cement sample analysis, optimum information is obtained from a received signal that is generated from a single, known surface and travels over a known, straight-line path.

BRIEF SUMMARY OF THE INVENTION

The preferred form of the cement testing method and apparatus of the present invention employs a single transducer, in contact with the sample, to both transmit and receive acoustic energy waves that are transmitted through a cement slurry sample and are reflected back to the transducer. The reflected signals are evaluated to determine various characteristics of the cement sample.

A single transducer design permits the use of a single pass-through fixture for electrical conductors entering the container holding the sample and the transducer. Designs employing multiple separate, spaced-apart transducers employ separate electrical access points through the container to contact the multiple transducers.

The pressurizing medium employed in the sample container of the present invention is water. The water may be placed in direct contact with the cement sample, thus eliminating the need for a flexible interface barrier. Because the pressurizing medium is water, which is a major component of the sample itself, there is no contamination of the sample, as might otherwise be present when a large surface area of cement is placed in contact with a pressurizing medium such as oil.

Each succeeding sample test requires only that the previous sample of cement and pressurizing water be removed and replaced with a new cement slurry sample and pressurizing water. Water is supplied to each new sample from an outside pressure source to provide the desired sample pressure. There is no requirement to dispose of pressurizing oil or to refill oil-containing protective areas, as is required in certain prior art designs. Use of a direct water-cement sample interface also eliminates the need for bleeding air from the space between the cement sample and a flexible diaphragm or other movable interfacing medium or structure.

The single transducer of the present invention is encapsulated within a sealed, variable volume, oil-containing protective housing that isolates the transducer and electrical connections from corrosive fluids and protects it from other damage that may result from direct contact with the water or the cement sample. The containing structure of the transducer housing is formed in part by a pressure-movable barrier that confines the oil in the housing while simultaneously reacting to the effects of water pressure applied against the barrier to communicate the water pressure to the contained oil. The movable barrier thus automatically provides for pressure equalization between the sample chamber and the transducer environment so that the transducer is pressure compensated during the testing procedure. Since the oil is sealed within the transducer housing, there is no requirement to dispose of oil used in each test, and there is no requirement to refill and bleed the oil-encapsulating area around the transducer.

The base of the transducer housing of the present invention is sealed with a thin metal sheet that physically separates the cement sample from the transducer structure. The oil contained within the transducer housing is also separated from the cement by the metal sheet. Pressure equalization between the oil-filled transducer housing and the cement sample prevents rupture of the thin metal sheet. The nominal thickness of the metal sheet prevents any significant attenuation of acoustic energy in the signal transmitted between the transducer and the sample. The result of all of these design features is that the transducer is in virtually direct physical contact with the cement sample and is protected within a sealed oil chamber that is pressurized to the same pressure as that being applied to the cement sample.

Proper transducer-to-cement coupling is obtained by immersing the base of the transducer slightly into the cement sample to ensure a proper transducer-to-cement interface free of water or other sample surface contamination. To this end, the transducer holder extends into the cement sample to hold the face of the transducer slightly below the surface of the cement slurry sample. The tip of the holder is frusto-conical to assist in permitting the holder to separate from a hardened cement sample. In one form of the invention, a temperature-responsive positioning spring automatically maintains the transducer face at a desired location against the sample as the sample temperature is changed.

Only a single air-bleed step is required for each test sequence since it is necessary to bleed the air out of the cement-containing test chamber only during the water-filing cycle of each test. By contrast, prior art systems require that both the transducer-containing area and the cement-containing area be bled free of air before a test sample may be safely pressurized and tested.

The quality of the received signal is enhanced by preventing damaging pressure differentials from acting across the body of the transducer, maintaining the transducer in proper contact with the sample during temperature and pressure changes, limiting the emitted sonic energy from the transducer to a primary signal, detecting a failure caused by water contact with the transducer's electrical lines and calibrating the transducer for use with the specific test chamber with which it is to be used.

From the foregoing, it will be appreciated that a primary object of the present invention is to provide a sample tester that analyzes a reflected sonic energy signal, which signal is transmitted and received by a single transducer, to obtain information about the sample through which the signal traveled.

Another important object of the present invention is to provide a cement slurry sample container that protects a single transducer within an oil-filled housing while maintaining the transducer in close physical contact with the cement sample as the sample is subjected to various pressure and temperature changes.

It is also an object of the present invention is to provide a cement slurry sample testing container that may be used to test successive samples without the need to bleed air from the fluid chamber protecting the transducer.

Yet another object of the present invention is to provide a cement slurry sample container in which the cement sample is pressurized by water in direct contact with the cement to eliminate the use of oil as a cement pressurizing medium and to prevent oil contamination of the cement sample, as well as to eliminate problems associated with disposal of the oil contaminated samples.

A general object of the present invention is to provide a cement sampling container that employs a minimum number of parts, using a single transducer as both a transmitting and a receiving device and permitting the use of a single electrical access through the sample container for both powering and monitoring the transducer.

It is yet another object of the present invention to provide a method for analyzing a cement slurry sample in which a reflected sonic signal is analyzed to obtain information regarding the setting time, compressive strength, and other physical characteristics of the sample.

An important object of the present invention is to provide a cement sample container in which a sonic energy signal transmitted from a transducer through the sample is free of signal distortion where such distortion may be caused by pressure differentials acting across components, by changes in temperature and pressure, by improper contact between the transducer and the sample, by secondary signals emitted from the transducer, by water contact with the transducer's electrical conduits, or by sample or container dimensions not properly correlated with the transducer and its configuration.

The foregoing, as well as other, objects, features, and advantages of the present invention will be better appreciated and understood by reference to the following drawings, specification, and claims.

DETAILED DESCRIPTION OF THE ILLUSTRATED EMBODIMENTS OF THE INVENTION

Figure 1:
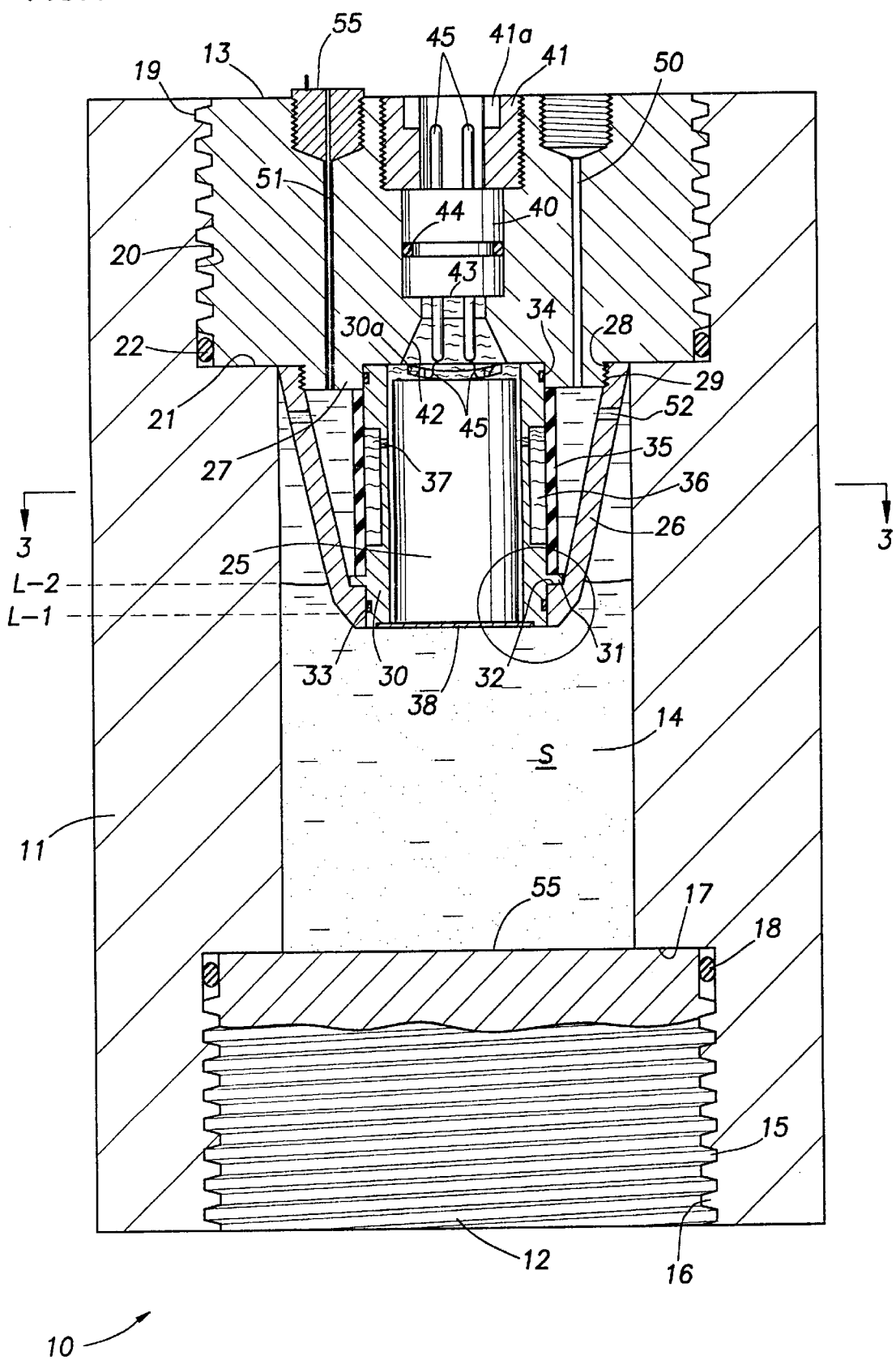
FIG. 1 is a vertical cross-sectional view of a sample container of the present invention.
Figure 3:
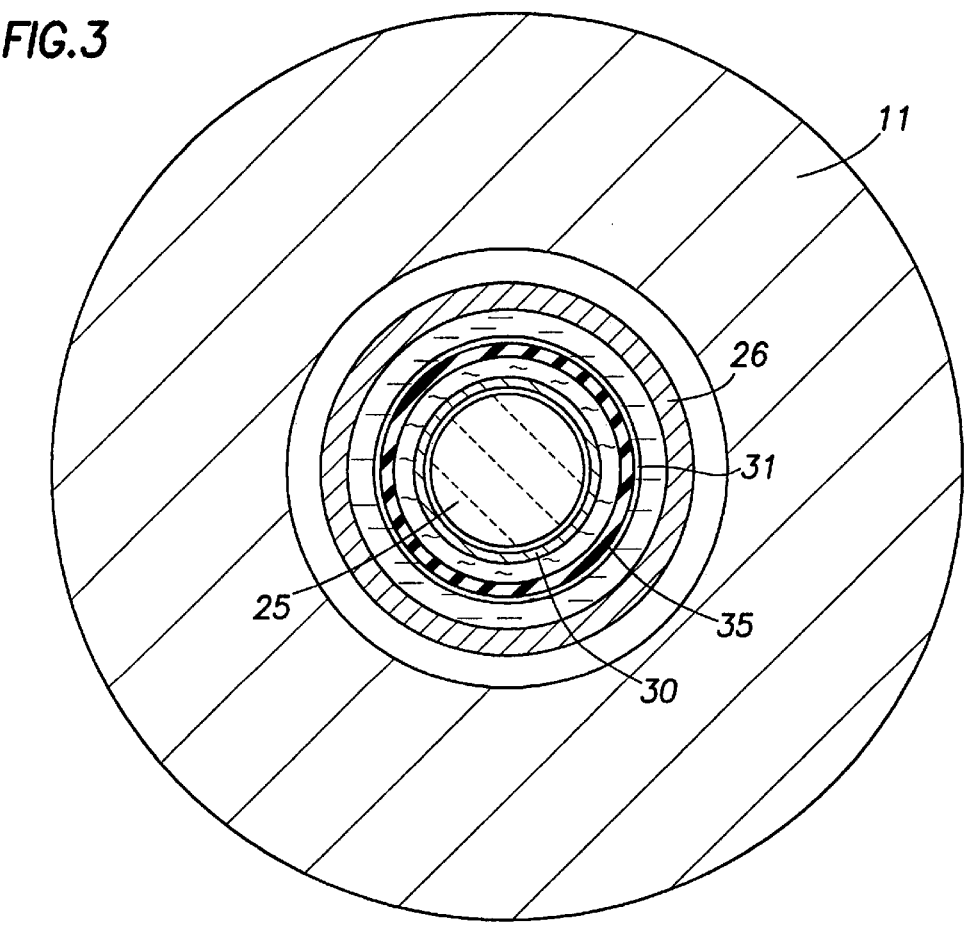
FIG. 3 is a horizontal cross-sectional view taken along the line 3—3 of FIG. 1.

A cement slurry sample container of the present invention is indicated generally at 10 in FIG. 1. As best illustrated by joint reference to FIGS. 1 and 3, the container 10 is comprised of a tubular body 11 that is closed at its lower end by a cylindrical bottom plug 12 and at its upper end by a cylindrical access cover assembly 13. The tubular wall 11, the lower cylindrical plug 12, and the cover assembly 13 define a fixed volume sample-containing cylindrical chamber area 14 that receives a cement slurry sample S. The body 11, plug 12, and cover assembly 13, as well as other metal components of the holder 10, hereinafter identified, are constructed of heat-treated stainless steel or other suitable material capable of withstanding repeated high pressure and high temperature test sequences. In the process of the test procedures, the container and its contents may be exposed to temperatures of 400° F. or higher and pressures of 20,000 psi or higher.

The bottom plug 12 is held in engagement with the body 11 by threads 15 formed along the external cylindrical surface of the plug. The threads 15 mate with threads 16 formed along the internal surface of the lower end of the tubular body 11. In its fully seated position in the body 11, the plug 12 engages an axial shoulder 17 formed at the base of the cylindrical chamber 14. An annular O-ring seal 18 formed of a suitable elastomeric material encircles the bottom plug 12 to provide a pressure-proof seal between the plug and the surrounding wall of the body 11. The O-ring seals and other elastomeric components of the sample holder 10 are preferentially constructed of a material that is capable of withstanding the high temperatures and pressures to which the holder is subjected. An example of such material is sold under the trademark Viton®. As will be understood, the plug 12 is rotated into and out of threaded engagement with the body 11 to respectively close or open the chamber area 14.

The access cover assembly 13 is provided along its outer circumferential surface with threads 19 that engage threads 20 formed along the internal circumferential surface of the upper end of the tubular body 11. The cover 13 seats against an axial shoulder 21 formed at the upper end of the cylindrical chamber 14. An elastomeric O-ring seal 22 is positioned between the cover 13 and the tubular body 11 to provide a pressure-tight seal between the two components.

A transducer assembly 25 is secured to the base of the cover 13 by a frustoconically shaped transducer holder 26. As used herein, the term "transducer assembly" is intended to include a single component transducer that can both generate and receive acoustic energy or multiple transducer components, each component of which either generates or receives acoustic energy. The holder 26 may be constructed of metal or other suitable material. The base of the cover 13 is provided with an axially extending cylindrical projection 27 having threads 28 along its external cylindrical surface. Threads 29 formed along the interior cylindrical base of the holder 26 interlock with the threads 28 to secure the holder to the cover 13. In the illustrated configuration, the access cover 13 and attached transducer holder 26 are removed from the tubular body 11 as a unit.

The transducer assembly 25 is contained within a tubular transducer housing sleeve 30 that is held between the base of the holder 26 and a cylindrical recessed area in the base of the cover 13. The housing sleeve 30, which is constructed of stainless steel, is secured against the holder 26 by engagement of an annular rim 31 that extends radially away from the housing sleeve body and rests against an internal axial shoulder 32 formed along the internal lower end of the holder 26. It will be appreciated that the rim 31 and the threaded engagement of the holder 26 to the base of the cover 13 axially confine the housing sleeve 30 within the holder 26. An annular elastomeric O-ring seal 33 provides a leak-proof contact between the base of the housing sleeve 30 and the internal opening at the lower end of the holder 26. A similar O-ring seal 34, positioned between the recessed area of the cover 13 and the opposite end of the transducer housing sleeve 30, provides a leak-proof seal between the housing sleeve and the cover.

Figure 2:
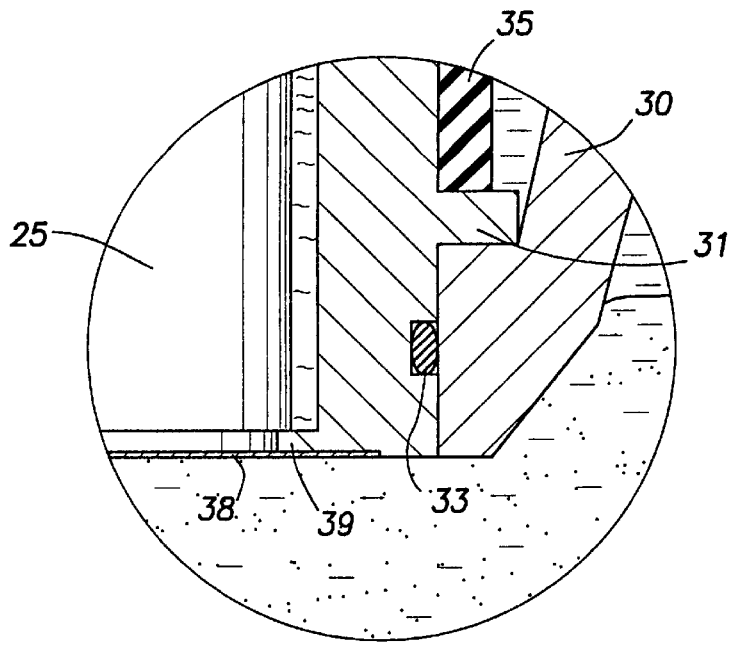
FIG. 2 is a vertical section of a portion of the sample container illustrating details in the construction of the protective transducer housing of the present invention.

A flexible tubular sleeve 35, constructed of Viton® or other suitable elastomeric material, is resiliently engaged about the external surface of the housing sleeve 30. An externally recessed annular area formed on the outer surface of the housing sleeve 30 cooperates with the flexible sleeve 35 to form a variable volume, annular chamber 36 for a purpose to be hereinafter described. Radial ports 37 communicate from the annular chamber 36 through the wall of the housing 30 sleeve to the central area within the housing sleeve 30 that holds the transducer assembly 25. The central area within the transducer housing sleeve 30 is sealed at the bottom of the housing sleeve by a thin sheet 38 of stainless steel or other suitable material. The sheet 38 is preferably 0.005" in thickness or less. As may best be described with reference to FIG. 2, the stainless steel sheet 38 is welded or otherwise suitably secured to the base of the housing 30 to provide a fluid seal covering the circular bottom opening of the tubular housing. The base of the transducer assembly 25 is supported against an internal lip 39 formed along the inner surface of the housing 30 to limit downward movement of the transducer through the housing. A wave spring 30a urges the transducer assembly against the sheet 38 to compensate for pressure and temperature-induced movement of the assembly 25. As will be more fully described, the sheet 38 protects the transducer from direct physical contact with material in the test chamber 14 without interfering with the proper functioning of the transducer 25.

The area between the cover 13 and the upper end of the housing 30 is sealed by a cylindrically shaped, high pressure electrical feedthrough connector 40. The connector 40, which may be constructed of stainless steel or other suitable material, is held in place by a retainer 41 in a central opening 42 formed through the cover 13. The retainer 41, constructed of stainless steel, is provided with threads along its external cylindrical surface that interlock with corresponding threads formed internally of the central opening 42 at the upper end of the cover 13. The retainer is provided with a tool recess 41a that receives a tool (not illustrated) for engaging and removing the retainer from the cover 13. The feedthrough connector 40 is constrained axially at its lower end by engagement with an axial shoulder 43 formed in the central opening 42. An elastomeric, O-ring seal 44 between the connector 40 and the cover 13 provides a pressure-tight seal between the two components. Insulated electrical conductors 45 extend through the feedthrough connector 40 with a pressure-tight seal to provide power and signal communication between the transducer and the external powering and analyzing circuitry (not illustrated).

The structure as thus described defines a variable volume, sealed oil encapsulation chamber that is used to encapsulate the transducer assembly 25 and the electrical conductors 45 to protect them from damaging contact with water or the cement sample. The oil encapsulation chamber is sealed by the cooperation of the connector O-ring seal 44, the housing O-ring seal 34, the tubular flexible sleeve 35, and the welded stainless steel sheet 38. The encapsulation chamber is filled with oil before the first test is performed. The oil is placed in the chamber through the central opening 42 provided in the cover 13, with the feedthrough connector 40 removed. Alternatively, the oil may be placed in the encapsulating area by injecting it between the rubber sleeve 35 and the housing 30 before the holder 26 is positioned to seat the housing against the base of the cover 13. Once the oil encapsulation chamber has been filled with oil and all air displaced from the chamber, the sample container may be used to test any number of samples without subsequent need for bleeding air from the oil chamber or refilling the chamber with oil.

The access cover 13 is provided with a high pressure access fill port 50 that is internally threaded at its upper end and extends axially through the cover 13 into the chamber 14. A similar high pressure port 51 that functions as an air bleed escape line and thermocouple connector also extends axially through the cover 13 into the sample chamber 14. Water is supplied to the sample chamber 14 through a high pressure supply line (not illustrated) that may be threaded into the opening of the access port 50. The water supplied through the port 50 communicates with the main portion of the sample chamber 14 through radial bores 52 formed in the holder 26.

In operation, the bottom plug 12 is screwed onto the tubular housing 11 and seated in the position illustrated in FIG. 1. With the top sealing assembly 13 and attached transducer assembly 26 removed, a cement slurry S is poured into the chamber 14 to approximately a level L-1. The tubular body 11 and bottom plug 12 are then threadedly secured to the cover 13, as illustrated in FIG. 1.

When the cover 13 is secured, as illustrated in FIG. 1, the holder 26 positions the lower end of the transducer 25 in the slurry sample S, which displaces the sample within the chamber 14 to a level L-2. This placement of the base of the transducer below the surface of the cement sample S ensures that the transducer is coupled with the cement material, below the level of any fluid overlying the slurry. The transducer holder 26 also penetrates the sample in a frustoconical form that assists in permitting separation of the holder from a cured cement sample after the testing has been completed.

Water is supplied to the closed chamber 14 through the port 50 with the port 51 opened to permit displaced air to escape from the chamber 14. Once all of the air has been displaced from the chamber 14, port 51 is closed by seating a thermocouple 55 in the threaded opening or by otherwise suitably closing the port 51.

The water supplied through the fill port 50 is pressurized by an external pressurizing mechanism (not illustrated) to bring the pressure within the chamber 14 to the desired testing pressure. At the same time as pressure is being applied to the sample, or at any time during the test procedure, the sample container 11 may be heated to the desired testing temperature in an autoclave or other suitable device (not illustrated). Temperature measurement of the sample may be performed by the thermocouple 55 positioned in the opening 51. The pressure of the water acting in the area above the sample S is communicated through the flexible sleeve 35 to the oil in the variable volume chamber encapsulating the transducer assembly 25. Because of the absence of air in the encapsulating oil-containing area, there is no significant physical distortion of the sleeve 35, and the absence of a pressure differential across the sleeve prevents any migration across the sleeve of water into the oil chamber or of oil into the water-containing area. The stainless steel sheet 38 is similarly pressure-balanced across the interface between the cement-containing area and the oil encapsulation chamber surrounding the transducer assembly 25. Accordingly, no damaging structural deformation acts on the steel sheet since there is no pressure differential across the sheet during the pressuring procedure.

During the testing process, electric pulses are delivered through the conductors 45 to the transducer assembly 25 to produce acoustic energy waves that emanate from the face of the transducer assembly 25 and travel through the sample S to a flat reflecting surface 55 formed on the inner surface of the plug 12. The reflected sound wave travels back to the transducer assembly 25, where it is converted to an electrical signal and conveyed through the conductors 45 back to the analyzing and processing circuitry.

Once a sample has been tested, the pressure in the chamber 14 is relieved and the housing 11 is unthreaded from the cover 13. With the housing 11 separated from the cover 13, the bottom plug 12 may be removed and the cured sample S knocked out of either end of the sample chamber 14. In some applications, it may be desirable to provide a tapering chamber that has its widest opening adjacent the cover 13. In such a construction, the sample would be extracted from the cover end of the housing.

The frustoconical form of the holder assists in withdrawing the cover assembly from the cured sample. While a frustoconical configuration is illustrated, it may be appreciated that separation is assisted by any configuration of the transducer holder that has a decreasing lateral dimension as it progresses axially from the surface of the sample toward the bottom of the sample. Once the sample is removed, the plug 12 may be reattached, another slurry sample placed in the chamber 14, and the previously described testing process repeated.

The transducer 25 is preferably a single transducer device that is capable of converting electrical energy into acoustic energy and also converting acoustic energy into electrical energy. One such transducer is manufactured and sold by Etalon as model no. RI-6010MIHPT-SL. This transducer has a nominal operating frequency of 500 kHz and a band width of 346 kHz with a 5 microsecond pulse width. In cement, the transducer has a useful operating frequency range of from about 100 kHz to 900 kHz. Measurements in the range of 50 kHz to more than 30 mHz may be made with other transducer assemblies.

Figure 4:
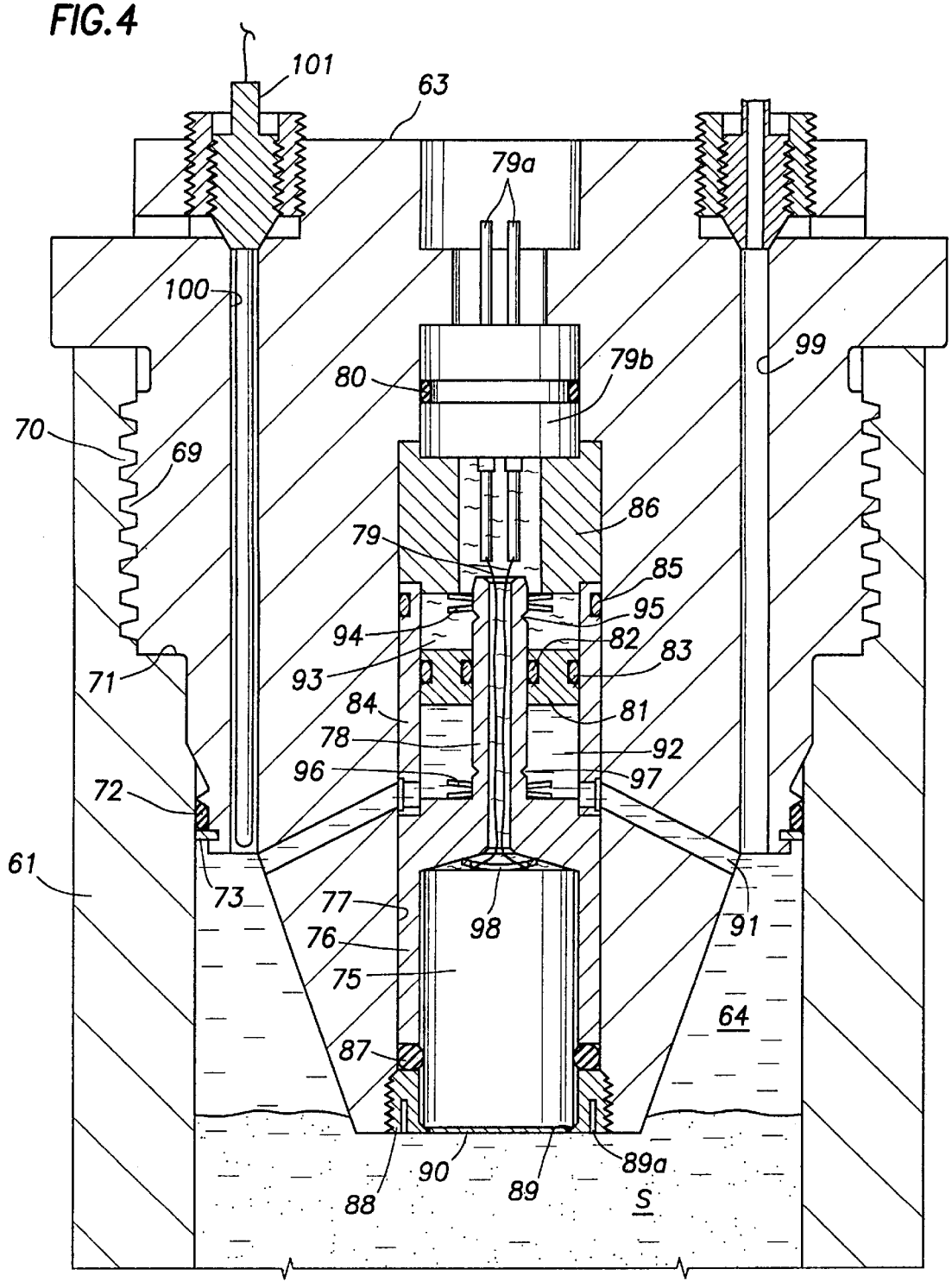
FIG. 4 is a vertical cross-sectional view of a modified sample container of the present invention.

A modified form of the access cover assembly employed in a sample-holding container of the present invention is indicated generally at 60 in FIG. 4. A tubular body section 61 (partially illustrated) is enclosed at its top by an access cover assembly 63 to confine a test chamber area 64. The cover assembly 63 is provided with threads 69 that engage threads 70 formed along the upper end of the tubular body 61. When fully engaged, the cover assembly 63 seats on an axial shoulder 71 that limits its downward travel. An O-ring seal 72 and a compression ring 73 between the cover assembly 63 and body 61 provide a pressure-tight seal between the engaged components.

A transducer 75 is secured centrally within the base of the cover assembly 63. The transducer 75 is held within a transducer holder 76 that in turn is contained within a central bore 77 extending axially through the body of the cover assembly 63. A tubular stem 78 extending upwardly from the cup-shaped base of the transducer holder 76 carries electrical transducer conductors 79 to electrical connectors 79a extending through a high pressure fixture 79b. An O-ring seal 80 between the connector fixture 79b and the surrounding wall of the central bore 77 forms a pressure seal at the upper end of the bore 77 that isolates the test area 64 from the ambient pressure outside of the cover 63. After passing through the connector fixture 79b, the connectors 79a are electrically contacted with the processing circuitry (not illustrated) used to excite and analyze the transducer signals.

Two pressure-equaling, variable volume areas are formed within the central bore 77 of the access cover 33 by a movable piston ring 81 that is sealingly and slidably engaged over the holder stem 78. An inner O-ring seal 82 between the piston ring 81 and the stem 78 provides a central sliding, sealing engagement that permits the seal ring to move axially up and down over the stem 78 while maintaining a sliding seal between the stem and seal ring. A larger seal ring 83 disposed along the outer circumferential surface of the piston ring 81, between the piston ring and a surrounding sleeve 84, provides a second sliding, sealing engagement surface between the seal ring and the sleeve.

The sleeve 84 is formed as a separate component from the transducer holder 76 to facilitate its construction. The upper end of the sleeve 84 is sealed within the central bore 77 by an O-ring seal 85. A spacer ring 86 at the upper end of the sleeve 84 holds the sleeve in place within the bore 77. The base of the sleeve 84 engages the cup-shaped section of the transponder holder 76 to limit the downward axial movement of the sleeve.

An O-ring seal 87 at the base of the holder cup section provides a pressure seal between the transducer 75 and the central bore 77 to seal the bottom of the central bore 77. A retaining bushing 88, threadedly engaged in the base of the bore 77 holds the entire assembly of transducer holder 76, sleeve 84, and spacer 86 axially fixed within the bore 77. An annular lip 89 formed along the base of the bushing 88 holds the transducer 75 in place within the base of the transducer holder 76. A thin membrane or sheet 90 of stainless steel or other suitable material, welded to the bushing 88, extends over the bottom surface of the bushing 88 and transducer 75 to prevent the transducer from contacting the fluid in the test chamber 64. The thickness of the membrane 90 is preferably only approximately 0.005" or less so that it will have little effect in attenuating signals emitted from, or received by, the transducer 75. Small recesses 89a are employed to a spanner wrench (not illustrated) for screwing the bushing into and out of the base of the bore 77.

Radially inclined access ports 91 extend from the test chamber 64 through the access cover 63 and sleeve 84 and into a water chamber 92 contained within the sleeve 84. The chamber 92 is sealed by the piston ring 81 from an oil chamber 93 on the opposite side of the piston ring.

The form of the invention illustrated in FIG. 4 includes provision to protect the transducer assembly from adverse effects caused by pressure- and temperature-induced conditions encountered during testing. The pressure-responsive protecting structure includes a wave washer assembly 94 secured at the upper end of the stem 78, immediately above a bypass groove 95 formed annularly about the stem 78. A similar arrangement is provided at the base of the stem 78 by a wave washer assembly 96 positioned immediately below an annular bypass groove 97 formed about the stem 78. A wave spring 98 positioned at the top of the transducer 75 to apply a constant biasing force against the transducer to keep the transducer seated on the bushing lip 89. The wave washer assemblies 94 and 96 and the wave spring 98 may be constructed of a suitable spring steel that will maintain the desired spring characteristics in the presence of the high temperature environments to which the washers and spring are exposed during the test procedure. As will hereinafter be more fully described, the piston ring 81 cooperates with the bypass grooves and wave washer assemblies to prevent a pressure differential from developing across the body of the transducer 75.

An access water fill port 99 extends axially through the access cover 63 for providing the pressurizing fluid to the sample. A similar access port 100 is provided for bleeding air from the test chamber 64 during the water fill procedure. After the air is bled from the chamber 64, a thermocouple 101 is screwed into the port 100 to monitor the sample temperature.

Corresponding components of the sample container 60 of FIG. 4 and the container 10 of FIG. 1 are constructed of similar materials. Thus, structural components of the sample holder 60 are constructed of heat-treated stainless steel while the elastomeric material of the O-ring seals is Viton®. As with the form of the holder illustrated in FIG. 1, the holder 60 of FIG. 4 must be constructed of materials that can withstand the pressure and temperature extremes encountered during the testing process.

The form of the invention illustrated in FIG. 4 operates in a manner similar to that of the embodiment described with reference to FIG. 1. With the access cover assembly 63 in place on the body 61, the container 61 is filled with a sample S to a level that will ensure that the frustoconical bottom termination of the closure assembly 63 will be slightly below the surface of the sample. Water is introduced into the chamber 64 through the water fill port 99 while the thermocouple 101 is removed from the passage 100. The water is added until all air in the container above the sample S is displaced, at which time the thermocouple 101 is engaged in the port 100 to seal the chamber 64. At this stage of the test sequence, the area of the chamber 64 above the cement is completely filed with water, as are the access ports 91 and the water chamber 92. The water in these areas is pressurized by the application of pressurized water supplied through the fill port 99. This pressure acts through the water into the chamber 92 to exert a displacing force, urging the piston ring 81 upwardly toward the oil chamber 93. The chamber 93 is devoid of air and is completely filled with a suitable oil that also fills the area confined centrally of the spacer 86, the center of the stem 78, and the area surrounding the transducer 75 above the lowermost seal ring 87. An oil-encapsulating chamber is thus defined at its lower end by the seal ring 87 engaging the transducer 75 and the cup section of the transducer holder and extending centrally through the central opening of the stem 78 and into the area above the stem to the seal 80 in the pass-through connector structure 79b. Movement of the piston ring 81 transfers the pressurizing force of the water in the water chamber 92 to the oil in chamber 93 so that equal pressures exist on either side of the piston ring 81. By this means, all of the elements encapsulated by the protective oil are maintained at the same pressure as the water but are protected from contact with the water.

As may be appreciated from the placement of the transducer 75 within the cover assembly 63, only the bottom surface or face of the transducer has direct communication with the sample. The sides of the transducer are isolated from the steel holder 76 and cover assembly 63 by a layer of oil that acts as a substantial attenuation of acoustic energy traveling through the surrounding steel structures. The transducer assembly 75 is also selected to be of a type having low sensitivity to acoustic energy entering from its side with the bulk of the material of the transducer assembly 75 adjacent the surrounding steel structures, providing extremely high attenuation of laterally directed acoustic energy. The result is that both the emitted and the received acoustic energy signals are concentrated at the transducer face and represent those signals propagating through the cement sample such that the signals are substantially free of extraneous, noise-producing energy components.

In the event of oil volume loss caused by high pressure compression of the oil or leakage through a portion of the assembly—for example, leakage of oil past the seal ring 80—the piston 81 will be permitted to move upwardly until the piston seal 82 registers with the bypass groove 95 on the stem 78. Once this occurs, the water is allowed to bypass the piston and flow into the area previously occupied by the oil. This expedient maintains pressure equalization across the body of the transducer, albeit at the expense of allowing water to come into contact with the electrical conductors 79. This latter condition, however, signals the occurrence of an anomaly and the need for corrective action before proceeding with the testing procedure.

In similar fashion, if the oil pressure in the chamber 93 exceeds that of the pressure in the water chamber 92, as might occur, for example, when the volume of the oil increases due to high temperatures or if water escaped from the water chamber 92 during testing, the piston 81 is driven downwardly until the O-ring seal 82 registers with the bottom bypass groove 97. At this point, the excess oil is drained from the oil chamber 93 by bypassing the oil across the seal 82, allowing it to escape into the water chamber and equalize the pressure across the piston 81. In each of the foregoing situations, the movement of the piston ring 81 into registry with one of the bypass grooves represents an abnormal condition that must be corrected before the testing can be properly completed. Allowing the system to bypass fluid rather than to continue a seal in the presence of a pressure differential protects the sensitive components of the system from damage.

Once the problem producing the pressure differential has been relieved from an abnormally operating or malfunctioning assembly, the wave washer assemblies 94 or 97, as the case may be, automatically move the piston ring away from the bypass groove 95 or 96 so that the seals of the piston ring are once again effective in isolating the oil chamber from the water chamber.

The spring washer 98 positioned between the top of the transducer 75 and the base of the cup section in the transducer holder 76 provides a constant biasing force that keeps the base of the transducer in contact with the cement sample to compensate for dimensional changes induced by pressure and temperature changes occurring during the testing of a sample.

Figure 5:
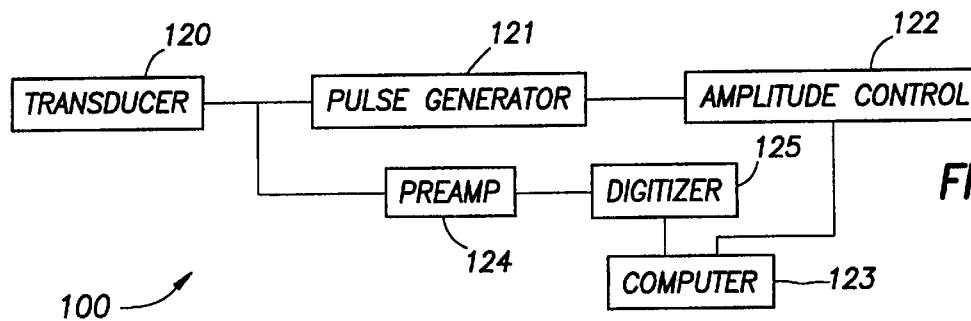
FIG. 5 is a schematic box diagram of an electrical circuit system for measuring physical characteristics of a cement slurry sample.

FIG. 5 of the drawings illustrates a schematic block diagram of an electrical system used with the sample testing structure of the present invention to determine characteristics of a cement sample. Indicated generally at 100, the system includes a transducer 120 (corresponding to the transducers 25 and 75 of FIGS. 1 and 4, respectively), which is supplied electrical power by a pulse generator 121. An amplitude control circuit 122 directs a computer 123 to control the signal amplitude generated by the transducer 120. The signal received by the transducer 120 is amplified by a preamplifier 124 to produce a voltage adequate for digitizing by a digitizer 125. The digitized signal is analyzed by the computer to measure the travel time of a reflected signal that is emitted from the face of the transducer to the bottom of the sample-containing chamber and returned to the transducer face.

Figure 6:
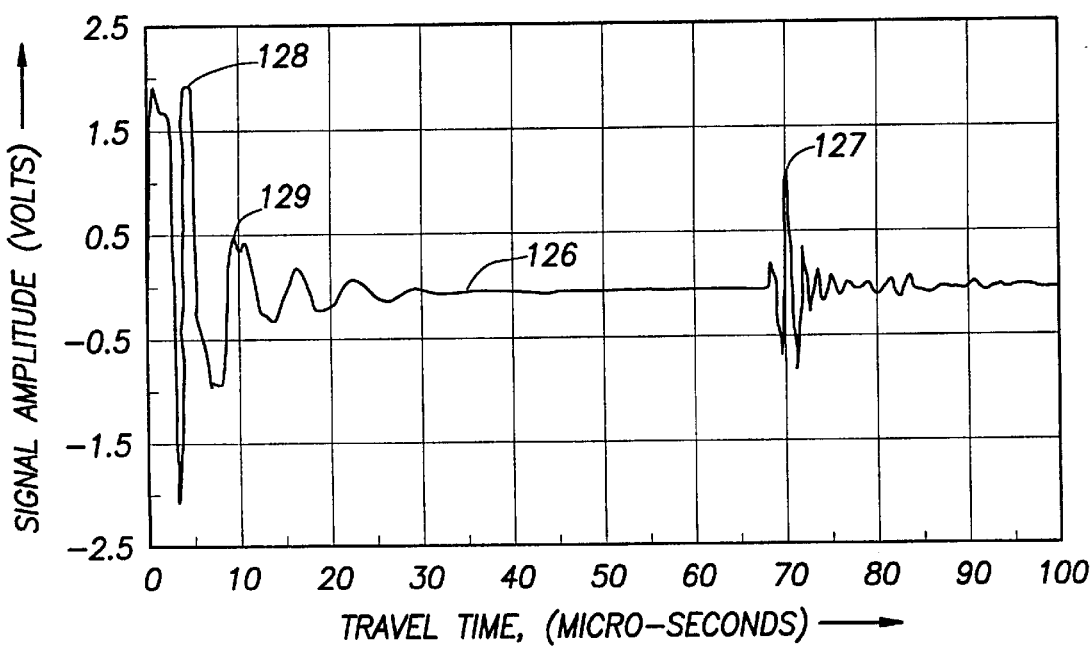
FIG. 6 is a graphical illustration of a typical reflected sonic energy signal produced and received by the method and apparatus of the present invention.

FIG. 6 of the drawings illustrates an example of the signal transmitted and received by a system constructed in accordance with the teachings of the present invention. The signal illustrated in FIG. 6 is representative of the signal amplitude (in volts) as a function of time (in microseconds) of the acoustic energy wave transmitted from the transducer face and reflected from the base of the sample container and received at the transducer face. Signal amplitude is plotted vertically, and time is plotted horizontally.

As depicted in FIG. 6, the first three microseconds of the acoustic energy signal, indicated at 126, represent an electrical transmit pulse 128 and a decay 124 of the energy in the transducer as a result of the process of generating the acoustic signal. The decay pulse is indicated in the interval between approximately 5 microseconds and 28 microseconds. At about 68 microseconds, a return signal 127, reflected from the bottom of the test cell, is detected by the transducer. The reflected signal detected by the transducer is converted to an electrical signal that is processed to measure the velocity of the acoustic energy signal in the test sample.

Figure 7:
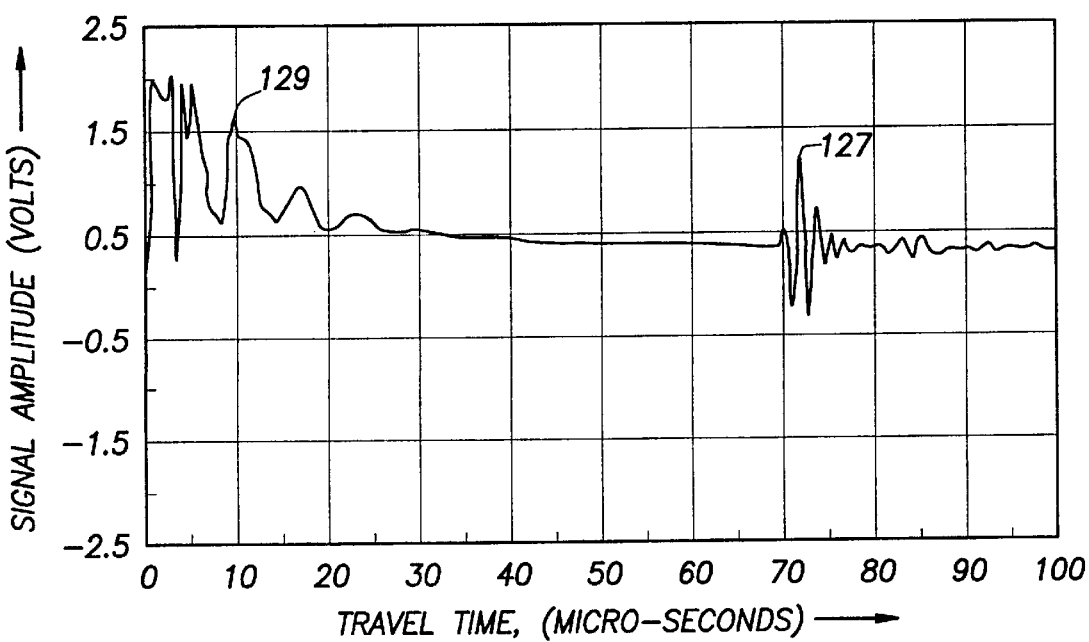
FIG. 7 is a graphical representation of a reflected sonic energy signal distorted as a result of water contact with the electrical lines connected with the transducer.

FIG. 7 of the drawings illustrates an acoustic energy signal similar to that illustrated in FIG. 6 as the signal might appear when the sample container has leaked, allowing water to come into contact with the electrical conductors associated with the transducer. The transmit pulse 128, decay signal 129, and reflected signal 127 correspond, respectively, to the same numbered components of the normal signal of FIG. 6. In the signal of FIG. 7, if the direct current (DC) component of the signal is measured in a window of from 10 microseconds to 20 microseconds, its value can be used to evaluated the presence of water across the transducer wires. As may be seen by reference to FIG. 6, the normal signal in FIG. 6 has very little DC offset whereas there is a significant DC offset in the signal illustrated in FIG. 7. This DC offset is a result of the wires' being wet with water. The signal condition of FIG. 7 is recognized by the system to warn of abnormal system operation. When the DC value has exceeded a specified value, the computer signals the operator that the transducer connectors are wet to alert the operators of the problems so that corrective action may be taken.

Figure 8:
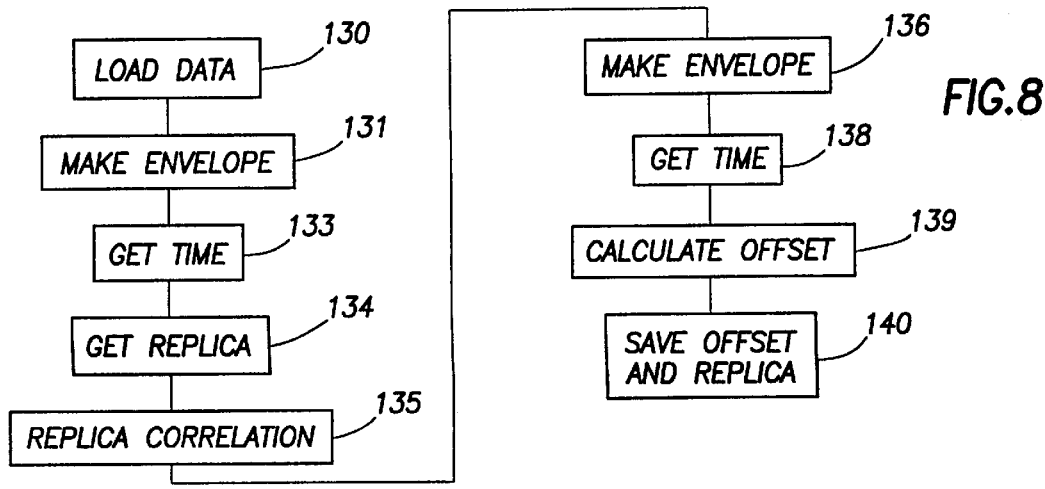
FIG. 8 is a schematic block diagram illustrating the calibration of the system of the present invention.

It will be appreciated that the sample container of the present invention may take on a variety of different physical configurations and may be used with a number of different transducers and transducer configurations. Proper evaluation of the information received by the transducer requires that each specific sample container configuration be properly correlated with the transducer to be employed in the test. FIG. 8 illustrates a schematic block diagram depicting a method for calibrating a sample testing chamber of the present invention. The test chamber is first filled with water in the chamber that is normally occupied by the cement sample. Water at a known temperature and pressure is employed as the calibrating medium because the velocity of sound in water at a specific temperature is well known and can thus be used as a reference in the test chamber. The steps of the calibration procedure include a first step 130 of loading the digitized calibration signal into a computer. Next, the envelope of the signal is computed 131. The arrival time of the reflected pulse is measured 133. The arrival time of the pulse is used to select the data points that correspond to the signal representing the echo from the bottom of the sample container vessel. This group of data points is used as a replica of the transducer signal, which is used as a basis for extracting noise from the actual sample measurements 134. A replica correlation is then performed on the original signal 135. The envelope of the result is computed 136, and the travel time is computed 138. The difference between the measured travel time and the expected travel time is used to compute the travel time offset 139. The travel time offset compensates processing electronic and mechanical effects that produce a fixed offset in the travel time measurement. The offset and the replica wave form are saved in a data file 140. The saved data file is used to measure the travel time in the sample with an unknown sound velocity to provide a calibrated measurement 140.

Figure 9:
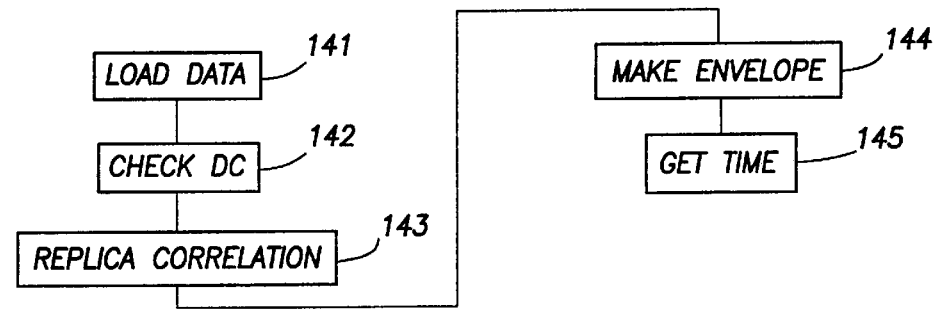
FIG. 9 is a schematic block diagram illustrating the measurement process of the present invention.

FIG. 9 illustrates the method for measuring the transit time of the acoustic energy wave through a sample of cement slurry. The procedure is similar to that used in the calibration process. The transmit pulse is initiated, and the reflected wave form is recorded into the computer 141. A check is made for water-wetting of the transducer conductors 142. If no wetness is indicated, the signal is correlated with a replica of the transducer signal measured during the calibration of the system 143. The envelope is obtained 144, and the travel time is then calculated 145.

Figure 10:
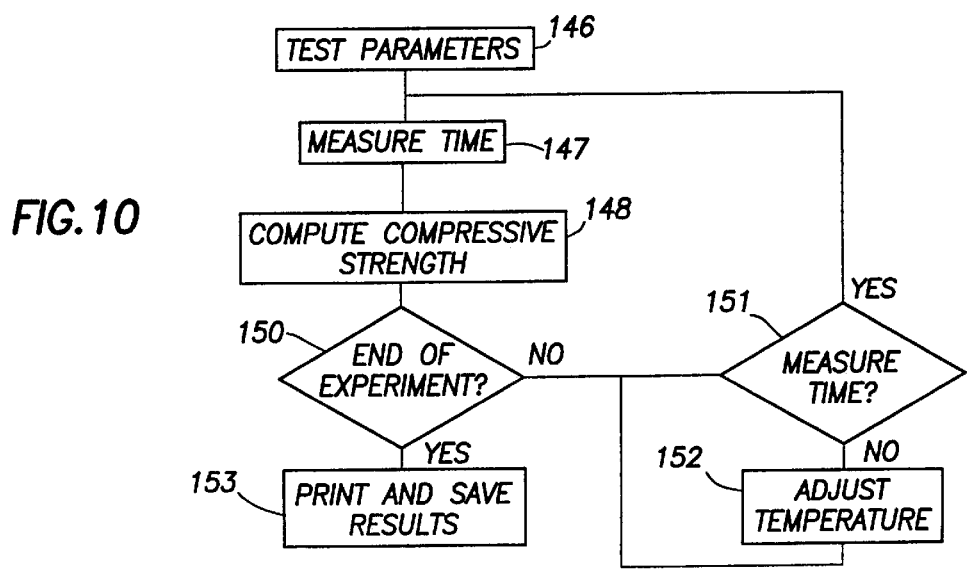
FIG. 10 is a schematic block diagram illustrating the steps in performing a test of a cement sample in the method and apparatus of the present invention.

FIG. 10 illustrates the process used in performing a cement test. Initially, the test operator inputs the parameters for the test to be conducted 146. These typically include duration of the test, sampling rate, and type of cement to be tested. A temperature and pressure profile are also established at this time for the test. The measurement process described previously with reference to FIG. 9 is then initiated by the computer 147. The computer uses the determined travel time to compute the compressive strength of the sample 148. The computer then checks to determine if the experiment has been completed 150. If the test has not been completed, the computer checks to determine if it is time to take a subsequent measurement 151. If it is not time for another measurement, the computer adjusts the temperature of the sample 152 and continues to monitor the temperature and time until it is time to take the next measurement. At this point, the computer loops back to 147 to continue the cycle. When the experiment is completed, the data is saved, and the result may be printed to a hard copy 153.

While specific forms of the invention have been described in detail herein, it will be appreciated that various changes in the form and practice of the invention may be made without departing from the invention. By way of example rather than limitation, the transducer assembly employed in the sample holder of the present invention may be a single transducer component or may be two separate transducer components. In a construction with two transducers, one transducer would provide the electrical-to-sonic energy transduction to generate the acoustic energy wave, and the other would provide the sonic-to-electrical transduction to receive the reflected acoustic signal. A system using a transmitting transducer and a separate receiving transducer that receives only a transmitted, non-reflected wave may also be benefitted by protecting the transducers in such a system from pressure differentials as taught by the present invention. Similarly, the direct positioning of the transducer face in the test medium while protecting the transducer from the effects of the corrosive material in the sample chamber has application to single or multiple transducer designs. It will also be appreciated that while the method of the present invention has been described for use in determining the compressive strength of a cured cement sample based on the velocity of the travel of a reflected sonic energy wave through an uncured slurry sample, the method may be used to determine other characteristics of cement or various other cured and uncured materials subjected to variations of temperature or pressure. Accordingly, it will be understood that the spirit and scope of the present invention is not limited to the specifically described embodiments but is rather defined by the following claims.

What is claimed is:

1. A material test device for testing material to be employed in an environment separate from said test device comprising:

a transducer assembly having at least one transducer component for converting electrical energy to acoustic energy and for converting acoustic energy to electrical energy;

a sample holder operatively connected with said transducer assembly;

a sample chamber in said sample holder for receiving and holding a sample of material that is to be tested;

a reflective surface included in said sample holder and spaced from said transducer assembly whereby acoustic energy waves transmitted from said transducer assembly travel through said sample chamber and are reflected from said reflective surface back through said sample chamber to said transducer assembly; and electrical circuitry operatively connected with said transducer assembly for supplying electrical power to said transducer assembly for producing acoustic energy waves and for receiving and analyzing electrical signals produced by said transducer assembly in response to reflected, acoustic energy waves.

2. A material test device as defined in claim 1 wherein said transducer assembly is at least partially disposed within said sample chamber for physical contact with a sample.

3. A material test device as defined in claim 1 wherein said transducer component is in communication with the pressure in said sample chamber.

4. A material test device as defined in claim 1 wherein said transducer component is encapsulated in a protective fluid that is sealed from said sample chamber.

5. A material test device comprising:

a transducer assembly having at least one transducer component for converting electrical energy to acoustic energy and for converting acoustic energy to electrical energy;

a sample holder operatively connected with said transducer assembly;

a sample chamber in said sample holder for receiving and holding a sample of material that is to be tested;

a reflective surface spaced from said transducer assembly whereby acoustic energy waves transmitted from said transducer assembly travel through said sample chamber and are reflected from said reflective surface back through said sample chamber to said transducer assembly;

electrical circuitry operatively connected with said transducer assembly for supplying electrical power to said transducer assembly for producing acoustic energy waves and for receiving and analyzing electrical signals produced by said transducer assembly in response to reflected, acoustic energy waves;

wherein said transducer component is encapsulated in a protective fluid that is sealed from said sample chamber; and a pressure-responsive barrier separating said protective fluid from said sample chamber for equalizing the pressure between said protective fluid and said sample chamber.

6. A material test device comprising:

a transducer assembly having at least one transducer component for converting electrical energy to acoustic energy and for converting acoustic energy to electrical energy;

a sample holder operatively connected with said transducer assembly;

a sample chamber in said sample holder for receiving and holding a sample of material that is to be tested;

a reflective surface spaced from said transducer assembly whereby acoustic energy waves transmitted from said transducer assembly travel through said sample chamber and are reflected from said reflective surface back through said sample chamber to said transducer assembly;

electrical circuitry operatively connected with said transducer assembly for supplying electrical power to said transducer assembly for producing acoustic energy waves and for receiving and analyzing electrical signals produced by said transducer assembly in response to reflected, acoustic energy waves; and a pressure-movable membrane disposed between said transducer component and said sample chamber for protecting said components from material in said sample chamber.

7. A material test device comprising:

a transducer assembly having at least one transducer component for converting electrical energy to acoustic energy and for converting acoustic energy to electrical energy;

a sample holder operatively connected with said transducer assembly;

a sample chamber in said sample holder for receiving and holding a sample of material that is to be tested;

a reflective surface spaced from said transducer assembly whereby acoustic energy waves transmitted from said transducer assembly travel through said sample chamber and are reflected from said reflective surface back through said sample chamber to said transducer assembly;

electrical circuitry operatively connected with said transducer assemble for supplying electrical power to said transducer assembly for producing acoustic energy waves and for receiving and analyzing electrical signals produced by said transducer assembly in response to reflected, acoustic energy waves; and wherein a single, pressure-tight pass-through connector is provided in said sample holder for connecting electrical conductors between said transducer assembly and said electrical circuitry.

8. A material test device as defined in claim 5 wherein:

said sample material is cement;

said protective fluid is oil; and said transducer component is held at one axial end of said chamber by an axially extending transducer holder that has a decreasing lateral dimension in an axial direction from said one axial end toward the opposite axial end of said chamber whereby said transducer holder may be separated from a solidified sample.

9. A material test device as defined in claim 1, further including a temperature-responsive biasing structure for retaining said transducer assembly in contact with a sample in said chamber.

10. A method of analyzing a material sample in a sample chamber wherein said sample chamber is a structure separate from the structure with which said material sample is to be employed, comprising the steps of:

placing said sample in a sample chamber;

transmitting an acoustic energy wave through said sample along a travel path to a reflecting surface wherein said reflecting surface is a part of the structure defining said sample chamber;

receiving a reflection of said acoustic energy wave from said reflecting surface; and evaluating said received, reflected acoustic energy wave to determine one or more characteristics of said sample.

11. A sample container for testing a fluid sample, comprising:

a containment structure enclosing a sample chamber;

an access cover assembly included in said containment structure for providing access to said sample chamber;

a transducer assembly in said sample chamber;

a transducer holder for holding said transducer assembly in contact with a sample in said sample chamber;

a protective fluid confined within said transducer holder and encapsulating said transducer assembly; and a movable, pressure-responsive barrier between said protective fluid and said sample chamber such that the pressure in said chamber and the pressure of said protective fluid are equalized whereby said transducer assembly is pressured to the same pressure as said sample chamber.

12. A method as defined in claim 10 wherein said acoustic energy wave is both transmitted and received by a single transducer component.

13. A method as defined in claim 10 wherein at least one transducer component is employed to transmit said acoustic energy wave and to receive said reflected acoustic energy wave.

14. A method as defined in claim 13 wherein said transducer component is pressure-equalized with said sample while transmitting and receiving acoustic energy waves.

15. A method as defined in claim 10, further comprising the steps of:

determining the speed of travel of an acoustic energy wave through a sample of uncured cement; and evaluating said speed of travel to determine the compressive strength of said cement sample when cured.

16. A method of analyzing a material sample, comprising the steps of:

placing a sample in a sample chamber;

transmitting an acoustic energy wave through said sample along a travel path to a reflecting surface wherein said reflecting surface is a part of the structure defining said sample chamber;

receiving a reflection of said acoustic energy wave from said reflecting surface;

evaluating said received, reflected acoustic energy wave to determine one or more characteristics of said sample;

changing one or more parameters affecting said sample for a period of time;

analyzing the acoustic energy wave received during said period of time; and correlating the analysis of said received acoustic wave with the one or more changed parameters.

17. A method as defined in claim 16 wherein said parameters comprise pressure and temperature.

18. A method of analyzing a material sample, comprising the steps of:

placing a sample in a sample chamber;

transmitting an acoustic energy wave through said sample along a travel path to a reflecting surface wherein said reflecting surface is a part of the structure defining said sample chamber;

receiving a reflection of said acoustic energy wave from said reflecting surface;

evaluating said received, reflected acoustic energy wave to determine one or more characteristics of said sample;

changing one or more parameters affecting said sample for a period of time;

analyzing the acoustic energy wave received during said period of time; and correlating the analysis of said received acoustic wave with the one or more changed parameters.

19. A method as defined in claim 12 wherein:

said sample chamber is defined by a sealable container that may be heated and pressurized;

said reflecting surface is a part of said container; and said transducer component operates at the pressure and temperature of said sample.

20. A method of analyzing a material sample, comprising the steps of:

placing a sample in a sample chamber;

transmitting an acoustic energy wave through said sample along a travel path to a reflecting surface wherein;

receiving a reflection of said acoustic energy wave from said reflecting surface;

evaluating said received, reflected acoustic energy wave to determine one or more characteristics of said sample wherein said acoustic energy wave is both transmitted and received by a single transducer component;

wherein said sample chamber is defined by a sealable container that may be heated and pressurized;

wherein said reflecting surface is a part of said container;

wherein said transducer component operates at the pressure and temperature of said samples; and wherein said transducer component is encapsulated by a protective fluid that is separated from the sample by a pressure-movable partition.

21. A method as defined in claim 20, further comprising the steps of:

changing one or more parameters affecting said sample for a period of time;

analyzing the acoustic energy wave received during said period of time; and correlating the analysis of said received acoustic wave with the one or more changed parameters.

22. A method as defined in claim 21 wherein said sample is an uncured cement.

23. A method of analyzing a material sample, comprising the steps of:

placing a sample in a sample chamber;

transmitting an acoustic energy wave through said sample along a travel path to a reflecting surface wherein said reflecting surface is a part of the structure defining said sample chamber;

receiving a reflection of said acoustic energy wave from said reflecting surface;

evaluating said received, reflected acoustic energy wave to determine one or more characteristics of said sample; and pressurizing said sample with water that is in direct contact with said sample.

24. A method as defined in claim 23, further comprising the step of evaluating said received signal for an abnormal condition existing in said sample chamber.

25. A sample container as defined in claim 11, further comprising a water supply port for supplying pressurized water to said sample chamber.

26. A sample container as defined in claim 11, further comprising a water supply port for supplying pressurized water into said sample chamber and into contact with a sample in said chamber.

* * * * *